United States Patent
Hoffman et al.

(10) Patent No.: US 11,810,662 B2
(45) Date of Patent: Nov. 7, 2023

(54) COLLECTION, STORAGE, AND MANAGEMENT OF IMAGES OR IMAGE RESULTS

(71) Applicant: IMAGEMOVERMD, INC., Madison, WI (US)

(72) Inventors: Jeffrey Hoffman, Madison, WI (US); Mark Gehring, Madison, WI (US); Brett Young-Moxon, Madison, WI (US); Kevin Houlihan, Madison, WI (US); Christopher Cash, Madison, WI (US); Shannon Goeldi, Madison, WI (US)

(73) Assignee: IMAGEMOVERMD, INC., Madison, WI (US)

( * ) Notice: Subject to any disclaimer, the term of this patent is extended or adjusted under 35 U.S.C. 154(b) by 0 days.

(21) Appl. No.: 17/687,292

(22) Filed: Mar. 4, 2022

(65) Prior Publication Data

US 2023/0282334 A1    Sep. 7, 2023

(51) Int. Cl.
| | | |
|---|---|---|
| *G16H 30/20* | (2018.01) | |
| *G16H 30/40* | (2018.01) | |
| *G16H 80/00* | (2018.01) | |
| *G16H 10/60* | (2018.01) | |

(52) U.S. Cl.
CPC ............ *G16H 30/40* (2018.01); *G16H 10/60* (2018.01); *G16H 30/20* (2018.01); *G16H 80/00* (2018.01)

(58) Field of Classification Search
CPC ........ G16H 30/40; G16H 10/60; G16H 30/20; G16H 80/00
See application file for complete search history.

(56) References Cited

U.S. PATENT DOCUMENTS

| | | | |
|---|---|---|---|
| 11,373,756 B1* | 6/2022 | Ferro, Jr. | G16H 40/63 |
| 2015/0370985 A1* | 12/2015 | Carvalko | G16H 10/60 705/2 |
| 2019/0311814 A1* | 10/2019 | Kannan | G16H 10/60 |
| 2021/0027885 A1* | 1/2021 | Averbach | G06Q 20/085 |
| 2021/0407675 A1* | 12/2021 | Kim | A61B 5/7267 |
| 2022/0020505 A1* | 1/2022 | Pulitzer | G06Q 10/10 |
| 2022/0084659 A1* | 3/2022 | Rowe | G06V 10/56 |
| 2022/0108439 A1* | 4/2022 | Dimov | G16H 50/20 |
| 2022/0236256 A1* | 7/2022 | Cooper-Phillips | G06T 7/0012 |
| 2022/0245800 A1* | 8/2022 | Champagne | G06F 3/013 |
| 2022/0254458 A1* | 8/2022 | Mooney | G06V 30/412 |

* cited by examiner

*Primary Examiner* — John R Downey
(74) *Attorney, Agent, or Firm* — Casimir Jones, S.C.; Kelly A. Barton

(57) ABSTRACT

The present disclosure provides methods, systems, and non-transitory computer-readable media for collecting, storing, assessing, and managing human readable diagnostic test results (e.g., results from Point-of-Care testing and self-testing). The present disclosure provides methods, systems, and non-transitory computer-readable media for collecting, storing, assessing, and managing images and image results. The systems and methods facilitate unbiased verification and notification of test and image results.

21 Claims, No Drawings

COLLECTION, STORAGE, AND MANAGEMENT OF IMAGES OR IMAGE RESULTS

FIELD

The present disclosure provides methods, systems, and non-transitory computer-readable media for collecting, storing, assessing, and managing images or image results (e.g., human readable diagnostic test results).

BACKGROUND

In the world of clinical patient care and public health, human readable diagnostic tests (e.g., rapid tests) provide fast, convenient, and accurate results, making them invaluable tools. During the COVID-19 pandemic, for instance, federal governments across the world have worked closely with industry to bring as many high quality tests to market as possible. Arguably, the most valuable of these rapid tests are antigen rapid tests. Human readable diagnostic tests can fall into two general classifications: Point-of-Care (POC) where the test is generally administered by another person and Over-the-Counter (OTC) where the test is designed to be administered by oneself. These tests can inform an average person in the populace if they are infected on demand and within a matter of minutes, leading them to make better health decisions for themselves, their families, and their communities. Recently, wider At-Home/OTC testing has been implicated as a key to success against the COVID-19 pandemic, even among vaccinated populations, but there is no infrastructure to support standard, unbiased testing at the necessary scale or turnaround time.

The evidence of the impact of these tests can be seen in the Emergency Temporary Standard (ETS) proposed in November 2021 by the Occupational Safety and Health Administration (OSHA). A central provision of the ETS requires certain employers to facilitate weekly COVID-19 antigen testing of their employees that are not fully vaccinated. There are several provisions as to which type of test will qualify, and room for interpretation, but one thing is clear to those that have read the guidelines: tests that are both collected and interpreted by the employee do not qualify under the ETS. However, this presents a difficult logistical challenge for employers and public health officials in how to test all of the potential individuals subject to the ETS prior to their scheduled work shift when they cannot administer their own OTC rapid test at home and how to handle the results in a secure and efficient manner.

SUMMARY

In some embodiments, the disclosure provides methods for collecting, storing, and managing images or image results. In some embodiments, the methods comprise receiving on an information processing component one or more images; transferring the one or more images to: a third-party device in contact with at least one image interpreter using a communication device within or in electronic communication with the information processing component wherein the at least one image interpreter determines an image result, an image analysis component and determining the test result using image analysis software, an artificial intelligence component and determining the test result using artificial intelligence component, or a combination thereof; and storing the image result. In some embodiments, the methods further comprise reporting the image result.

This disclosure relates, in some embodiments, to computer implemented methods for collecting, storing, and managing human readable diagnostic test results (e.g., Point-of-Care and self-test results) for a subject.

In some embodiments, the methods comprise collecting demographics, symptoms, exposure details, or a combination thereof from the subject, receiving a test result for the subject, and storing the test result. In some embodiments, the collecting comprises querying the subject in a protocol component. In some embodiments, the collecting comprises identifying the subject demographics from an identification number, access code, or list of potential subjects. In some embodiments, the methods further comprise associating the test result with the subject.

In some embodiments, the test result is provided by the subject or a test administrator. In some embodiments, receiving the test result comprises receiving on an information processing component, from a subject device or a test administrator device, one or more images of a test kit following use and test kit identification, and transferring the image(s) to a third-party device in contact with at least one image interpreter (e.g., an interpretation expert) using a communication device within or in electronic communication with the information processing component wherein the at least one image interpreter determines the test result, transferring the image(s) to an image analysis component and determining the test result using image analysis software, and/or transferring the image to an artificial intelligence component and determining the test result using artificial intelligence component. In some embodiments, the test result is a consensus result from at least three (e.g., 3, 5, 7, 10, 20, 50, 100, 200, 500, 1000) image interpreters. In some embodiments, the test result is a consensus result from more than one image interpreter as determined by a set of adjudication rules.

In some embodiments, the methods comprise: collecting demographics, symptoms, exposure details, or a combination thereof from the subject; receiving a test result from the subject or a test administrator; and/or receiving on an information processing component, from a subject device or a test administrator device, one or more images of a test kit following use and test kit identification; and transferring the one or more images to a third-party device in contact with at least one image interpreter (e.g., an interpretation expert) using a communication device within or in electronic communication with the information processing component wherein the at least one image interpreter determines the test result, or transferring the one or more images to an image analysis component and determining the test result using image analysis software, and/or transferring the one or more images to an artificial intelligence component and determining the test result using artificial intelligence component; associating the test result with the subject; and storing the test result.

In some embodiments, the methods further comprise providing the test result to the subject. In some embodiments, the methods further comprise reporting the test result to governmental or central (e.g., state and/or federal) health authorities.

In some embodiments, the methods further comprise collecting subject medical history. In select embodiments, the medical history comprises vaccination records.

The disclosure also relates to non-transitory computer-readable medium storing instructions and instructions configured to carry out the disclosed methods. The disclosure additionally provides methods for assessing images and image results. In some embodiments, the methods comprise loading one or more images into an information processing component and receiving an image result from the information processing component, wherein the one or more images are sent to a third-party device in contact with at least one image interpreter using a communication device within or in electronic communication with the information processing component and the at least one image interpreter determines the image result. The methods may further comprise capturing an image on an imaging device.

In some embodiments, the one or more images are sent to a third-party device in contact with at least one image interpreter using a communication device within or in electronic communication with the information processing component and the at least one image interpreter determines the result. In some embodiments, at least three image interpreters determine the result. In some embodiments, the result is a consensus result from the at least three image interpreters. In some embodiments, the test result is a consensus result from more than one image interpreter as determined by a set of adjudication rules.

In some embodiments, the information processing component determines the test result using image analysis software. In some embodiments, an artificial intelligence component determines the test result.

The disclosure further relates to methods for assessing human readable diagnostic test results. In some embodiments, the methods comprise capturing one or more images of a test kit following use on an imaging device, loading the one or more images into an information processing component from the imaging device, and receiving test results from the information processing component.

In some embodiments, the one or more images are sent to a third-party device in contact with at least one image interpreter using a communication device within or in electronic communication with the information processing component and the at least one image interpreter determines the test result. In some embodiments, at least three image interpreters determine the test result. In some embodiments, the test result is a consensus result from the at least three image interpreters.

In some embodiments, the information processing component determines the test result using image analysis software. In some embodiments, an artificial intelligence component determines the test result.

In some embodiments, the methods further comprise providing or selecting subject demographics, symptoms, exposure details, or a combination thereof to a protocol component of the information processing component. In some embodiments, the methods further comprise receiving guidance or instructions from a protocol component.

The disclosure also relates to systems for carrying out the disclosed methods. In some embodiments, the systems comprise an imaging device, a communication component, an information processing component, and a protocol component. In some embodiments, the imaging device is a digital camera. In some embodiments, the imaging device is integrated into the information processing component. In some embodiments, the communication component is a wireless communication component.

In some embodiments, the information processing component is a tablet computer or a portable computer. In some embodiments, the information processing component is in communication with a third party device in contact with at least one image interpreter. In some embodiments, the information processing component comprises image analysis software to analyze images received from the imaging device.

Other aspects and embodiments of the disclosure will be apparent in light of the following detailed description.

DETAILED DESCRIPTION

Traditional tests often require long wait times for test administration or results from the laboratory in which the test is sent for analysis. Human readable diagnostic tests are used by thousands every day to speed up testing and analysis. Wider OTC testing has been implicated as a key to success against the Covid-19 pandemic, even among vaccinated populations, but the infrastructure to support independently read testing, at the scale that is needed or with the turnaround time that is even effective, does not exist.

The present disclosure provides methods, systems, and non-transitory computer-readable media for collecting, storing, assessing, and managing human readable diagnostic test results, particularly Point-of-Care (POC) or self-test (e.g., Over-the-Counter (OTC) tests) which result in increased quality of test results, lower costs, and faster turnaround times. The increased quality is provided, in part, because an individual taking a test at home is allowed to collect the specimen but is not the sole interpreter of the result. The disclosed methods and systems provide a platform for a subject or test administrator to conduct the test and securely enter and track the test results. Image analysis software or image classification experts (e.g., through a crowdsourcing platform) may be used to digitally interpret the photo of a sample that is collected and performed by the individual taking the test as a primary means of determining the result or verification of the result as determined by the subject or a test administrator.

Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined herein, scientific, and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

A "subject" may be human or non-human and may include either adults or juveniles (e.g., children). Moreover, subject may mean any living organism, preferably a mammal (e.g., human or non-human). Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. In one embodiment of the methods and compositions provided herein, the mammal is a human.

Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

Computer Implemented Methods

The present disclosure provides for collecting, storing, and managing images and image results. The methods comprise receiving on an information processing component one or more images, transferring the one or more images to a third-party device in contact with at least one image interpreter using a communication device within or in electronic communication with the information processing component wherein the at least one image interpreter determines an image result, transferring the one or more images to an image analysis component and determining the test result using image analysis software, and/or transferring the one or more images to an artificial intelligence component and determining the test result using the artificial intelligence component; and storing the image result. In some embodiments, the methods further comprise reporting the image result (e.g., to a client or third party). In some embodiments, the images or image results comprise human readable diagnostic tests or results thereof.

The present disclosure also provides for collecting, storing, and managing human readable diagnostic test results. The methods comprise collecting demographics, symptoms, exposure details, or a combination thereof from the subject, receiving a test result for the subject, storing the test result. In some embodiments, the human readable diagnostic test results are for diagnosis of an infection (e.g., an infection with influenza virus or coronavirus). However, the technology may be used with any type of testing, including, but not limited to, blood glucose tests, cancer biomarker tests, metabolic disease tests, inflammation biomarker tests, heart disease biomarker tests, drug tests, genetic tests, organ function tests, metabolite tests, and the like.

A protocol component may instruct the subject with a series of questions or prompts to enter in the desired information regarding demographics, symptoms, and/or exposure details. Exemplary symptoms include reporting any symptoms related to the disease or illness, including but not limited to, chills, cough, diarrhea, fatigue, fever, headache, loss of taste or smell, breathing difficulty, nasal congestion, nausea, runny nose, sore throat, and the like. Exemplary exposure details include test history, hospitalization for related illness, high risk living situations, travel details, close contact to others with a confirmed or expected diagnosis, high risk conditions, or any combination thereof.

The subject demographics may include a first name, a last name, if applicable, a maiden or previous name, date of birth, sex, race or ethnicity, address, contact information and preferences, or any combination thereof. In some embodiments, collecting the demographics may comprise querying the subject in the protocol component. Alternatively, or in addition, the demographic information may also be collected from an identification number, access code, or list of potential subjects. For example, the subject identification number may be a driver's license number or an access code provided by a medical provider. The demographic information may also be gathered from a scanned image of a provided form of identification (e.g., driver's license or passport).

In some embodiments, the test result may be provided by the subject or a test administrator. Alternatively, or additionally, the test result may be provided by independent analysis of the test kit result (e.g., by a third-party or computer-aided analysis).

In some embodiments, receiving the test result comprises receiving on an information processing component, from a subject device or a test administrator device, one or more images of a test kit following use and test kit identification. The images may be in any image format (e.g., JPEG, GIF, PNG, or other image format) or non-image format (e.g., PDF files). The subject device or test administrator device may be a device with an integrated imaging device in communication with the information processing component.

In some embodiments, the image(s) are transferred to a third-party device in contact with at least one image interpreter using a communication device within or in electronic communication with the information processing component wherein the at least one image interpreter determines the result.

In some embodiments, the desired number of image interpreters is variable and determined by a set of adjudication rules. For example, the adjudication rule set may be designed to minimize the risk of false positive or false negative test results, to handle low quality or complex images, and/or select a highly-trained set of interpreters or exclude less experienced interpreters for certain images or test results. In some embodiments, the adjudication rules facilitate the determination of a consensus result and include, for example, determination of an initial number and type of interpreters, addition of interpreters when a desired percent consensus is not reached, and/or determination of unusable or invalid results based on initial or subsequent results from a set number of interpreters. Use of an exemplary set of adjudication rules was shown to increase the accuracy of the results from about 70% with a random selection of interpreters to greater than 99% using the adjudication rules.

In some embodiments, the test result is a consensus result from the at least three image interpreters. For example, in order for a certain result (e.g., positive or negative test result) to be verified multiple (e.g., three or more) independent image interpreters need to agree on the result.

The thresholds for a consensus result can be set based on a variety of factors (e.g., the test kit being used and the presumptive result). For example, a positive test result may require more independent interpreters to agree versus a negative result. Additionally, if a test kit or batch of test kits is faulty (e.g., high level of false positives or negatives) the result may be flagged as likely invalid based on feedback from other test results. If the threshold is set and the results set from interpreters do not meet that threshold, no result will be provided as a consensus was not reached.

In some embodiments, the result or consensus results are determined by the interpreter(s) in less than one hour (e.g., less than 30 minutes, less than 20 minutes, less than 10 minutes, or less than 5 minutes).

The subject device, administrator device, or third-party device may be a desktop computer, a laptop, a tablet computer, a smartphone, or similar computer device that is configured to allow integration with the information processing component.

In some embodiments, the image is transferred to an image analysis component and the test result is determined using image analysis software. In some embodiments the image analysis software evaluates the image and may also generate results and/or reports based on the analysis of the image.

The image analysis software may include the ability to transform the images provided by the subject, creating enhanced images which may include highlighting, coloring, emphasis or de-emphasis of detail, digital filtering, among many other potential transformations. The software could be custom designed, licensed from third parties, or even commercially available software. Multiple software programs may be utilized together in order to fully analyze the image.

In some embodiments, the information processing component comprises an artificial intelligence component (e.g., embodied in software running on the processor). In some embodiments, the image is transferred to the artificial intelligence component and the result is determined by the artificial intelligence component. In some embodiments, the artificial intelligence component instructs the information processing component to report the results. In some embodiments, the artificial intelligence component will go through a machine learning process, both supervised and unsupervised.

In some embodiments, the image(s) are transferred to any combination of the at least one image interpreter, the image analysis component, and the artificial intelligence component and the result is determined by the combination thereof. For example, the image(s) may be transferred to at least one image interpreter and the artificial intelligence component and the result is determined by the combination.

In some embodiments, the image analysis software transforms the images prior to transfer to at least one image interpreter and/or the artificial intelligence component for result determination. In some embodiments, the image analysis software determines or assists in determining the result.

In some embodiments, the adjudication rules may determine if the image analysis component and/or the artificial intelligence component should be included in the image analysis to reach a consensus result.

In some embodiments, the methods further comprise associating the test result with the subject. For example, in some embodiments a test administrator may associate a particular test kit or cartridge with a subject demographics by means of a barcode or other numerical identifier. Once the test has developed the administrator may associate the test result with the subject using the barcode or numerical identified without having any subject demographic or health information on hand. As such, any means of associating the test result with the subject outside of subject demographic or health information is suitable for use with the disclosed methods.

In some embodiments, the methods comprise: collecting demographics, symptoms, exposure details, or a combination thereof from the subject; receiving a test result from the subject or a test administrator; and/or receiving on an information processing component, from a subject device or a test administrator device, one or more images of a test kit following use and, optionally, test kit identification; and transferring the image to a third-party device in contact with at least one image interpreter using a communication device within or in electronic communication with the information processing component wherein the at least one image interpreter determines the test result, transferring the one or more images to an image analysis component and determining the test result using image analysis software, and/or transferring the one or more images to an artificial intelligence component and determining the test result using the artificial intelligence component; associating the test result with the subject; and storing the test result.

In some embodiments, the methods further comprise providing the test result to the subject. The subject can choose by what method(s) the test result can be provided, including, for example, email, text messaging, and phone message.

In some embodiments, the methods further comprise reporting the test result to a central health care facility or a governmental organization (e.g., state and/or federal health authorities). Reporting the test results may comprise sorting, updating, and exporting results to match the required output for a given health agency depending on the location the result was collected or the location of the subject who was tested.

In some embodiments, the methods further comprise collecting subject medical history. The medical history may include past diagnoses of the tested disease or condition or related conditions, medical conditions which result in the subject being high risk, family history, vaccination records, and the like. In select embodiments, the medical history comprises vaccination records. The vaccination records may be uploaded with an image of the vaccination card or confirmation.

The methods described herein can be implemented in digital electronic circuitry, or in computer software, firmware, or hardware. The methods can be implemented as one or more computer programs, e.g., one or more modules of computer program instructions, encoded on computer storage medium for execution by, or to control the operation of, data processing apparatus. Alternatively, or in addition, the program instructions can be encoded on an artificially generated, propagated signal, for example, a machine-generated electrical, optical, or electromagnetic signal that is generated to encode information for transmission to suitable receiver apparatus for execution by a data processing apparatus. In some embodiments, the methods are implemented as a non-transitory computer-readable medium storing instructions executable by one or more processors to perform operations.

The present disclosure also provides non-transitory computer-readable media. The non-transitory computer-readable media stores instructions that when executed by one or more processors performs some or all of the operations described in the disclosed methods.

In some embodiments, the one or more processors perform operations comprising at least one or all of: receiving on an information processing component an image; transferring the image to a third-party device in contact with at least one image interpreter using a communication device within or in electronic communication with the information processing component wherein the at least one image interpreter determines the test result, transferring the image to an image analysis component and determining the test result using image analysis software, and/or transferring the image to an artificial intelligence component and determining the test result using the artificial intelligence component; and storing the test result. The processors may further perform operations of reporting the image result.

In some embodiments, the one or more processors perform operations comprising at least one or all of: collecting demographics, symptoms, exposure details, or a combination thereof from a subject; receiving a test result for the subject; and storing the test result. The processors may further perform any or all of the operations of: querying the subject in a protocol component; identifying the subject demographics from an identification number, access code, or list of potential subjects, or a combination thereof; receiving on an information processing component, from a subject device or a test administrator device, an image of a test kit following use and test kit identification; transferring the image to a third-party device in contact with at least one image interpreter using a communication device within or in electronic communication with the information processing component wherein the at least one image interpreter determines the test result; transferring the image to an image analysis component and determining the test result using image analysis software; associating the test result with the subject; providing the test result to the subject; reporting the test result to state and federal health authorities; and collecting subject medical history.

The methods described herein can be implemented as a system including one or more processors and a computer-readable medium storing instructions executable by the one or more processors to perform operations, as described above. The system may comprise at least one computer system comprising the one or more processors and/or the computer-readable media. The system may further comprise one or more local servers or databases connected to or integrated with the one or more computer systems. The system may further comprise one or more devices integrated with the computer systems. For example, the devices may include a user device configured to allow a user (e.g., a subject, test administrator) to access and use the computer system.

Assessing or Verifying Test Results

The present disclosure further provides methods and systems to assess images and image results. The methods comprise loading an image into an information processing component and receiving image result from the information processing component, wherein the image is sent to a third-party device in contact with at least one image interpreter using a communication device within or in electronic communication with the information processing component and the at least one image interpreter determines the image result. In some embodiments, the methods may further comprise capturing an image on an imaging device.

The present disclosure further provides methods and systems to assess human readable diagnostic test results for a subject. In some embodiments, the human readable diagnostic test results are for diagnosis of an infection (e.g., an infection with influenza virus or coronavirus).

The methods comprise capturing an image of a test kit following use on an imaging device; loading the image into an information processing component from the imaging device; and receiving test results from the information processing component.

In some embodiments, the image is sent to a third-party device in contact with at least one image interpreter using a communication device within or in electronic communication with the information processing component and the at least one image interpreter determines the result. In select embodiments, at least three image interpreters determine the result. In some embodiments, the result is a consensus result from the at least three image interpreters. For example, in order for a certain result (e.g., positive or negative test result) to be verified multiple (e.g., three or more) independent image interpreters need to agree on the test result.

The thresholds for a consensus result can be set on a variety of factors (e.g., the test kit being used and the presumptive result). For example, a positive result may require more independent interpreters to agree versus a negative result. Additionally, if a test kit or batch of test kits is faulty (e.g., high level of false positives or negatives) the result may be flagged as likely invalid based on feedback from other test results. If the threshold is set and the results set from interpreters do not meet that threshold, no result will be provided as a consensus was not reached.

In some embodiments, the desired number of image interpreters is variable and determined by a set of adjudication rules. For example, the adjudication rule set may be designed to minimize the risk of false positive or false negative test results, to handle low quality or complex images, and/or select a highly-trained set of interpreters or exclude less experienced interpreters for certain images or test results. In some embodiments, the adjudication rules facilitate the determination of a consensus result and include, for example, determination of an initial number and type of interpreters, addition of interpreters when a desired percent consensus is not reached, and/or determination of unusable or invalid results based on initial or subsequent results from a set number of interpreters. Use of an exemplary set of adjudication rules was shown to increase the accuracy of the results from about 70% with a random selection of interpreters to greater than 99% using the adjudication rules.

In some embodiments, the result or consensus results are determined by the interpreter(s) in less than one hour (e.g., less than 30 minutes, less than 20 minutes, less than 10 minutes, or less than 5 minutes).

In some embodiments, the information processing component determines the test result using image analysis software. In some embodiments the image analysis software evaluates the image and may also generate results and/or reports based on the analysis of the image.

The image analysis software may include the ability to transform the images provided by the subject, creating enhanced images which may include highlighting, coloring, emphasis or de-emphasis of detail, digital filtering, among many other potential transformations. The software could be custom designed, licensed from third parties, or even commercially available software. Multiple software programs may be utilized together in order to fully analyze the image.

In some embodiments, the information processing component comprises an artificial intelligence component (e.g., embodied in software running on the processor). In some embodiments, the image is transferred to the artificial intelligence component and the result is determined by the artificial intelligence component. In some embodiments, the artificial intelligence component instructs the information processing component to report the results. In some embodiments, the artificial intelligence component will go through a machine learning process, both supervised and unsupervised.

In some embodiments, the image is transferred to any combination of the at least one image interpreter, the image analysis component, and the artificial intelligence component and the result is determined by the combination thereof. For example, the image may be transferred to at least one image interpreter and the artificial intelligence component and the result is determined by the combination.

In some embodiments, the image analysis software transforms the images prior to transfer to at least one image interpreter and/or the artificial intelligence component for result determination. In some embodiments, the image analysis software determines or assists in determining the result.

In some embodiments, the adjudication rules may determine if the image analysis component and/or the artificial intelligence component should be included in the image analysis to reach a consensus result. In some embodiments, the method further comprises providing or selecting subject demographics, symptoms, exposure details, or a combination thereof to a protocol component of the information processing component. The protocol component may instruct the subject over a series of questions or prompts to enter in the required or requested information regarding demographics, symptoms, exposure details. Exemplary symptoms include reporting any symptoms related to the disease or illness, including but not limited to, chills, cough, diarrhea, fatigue, fever, headache, loss of taste or smell, breathing difficulty, nasal congestion, nausea, runny nose, sore throat, and the like. Exemplary exposure details include test history, hospitalization for related illness, high risk living situations, travel details, close contact to others with a confirmed or expected diagnosis, high risk conditions, or any combination thereof.

The subject demographics may include a first name, a last name, if applicable, a maiden or previous name, date of birth, sex, race or ethnicity, address, contact information, or any combination thereof. In some embodiments, the protocol component may query the subject regarding the desired demographic information. Alternatively, or in addition, the subject may provide demographic information from an identification number, access code, or list of potential subjects. For example, the subject identification number may be a driver's license number or an access code provided by a medical provider. The demographic information may also be gathered from a scanned image of a provided form of identification (e.g., driver's license or passport).

In some embodiments, the systems and methods comprise one or more or each of: an imaging component, a communication component, an information processing component, and a protocol component.

Imaging Device

In some embodiments, the systems and methods comprise an imaging device. The imaging device facilitates capture of an image(s) of (e.g., test kit results, and optionally an image of the test kit itself for use verifying the manufacturer's instructions for analysis).

The imagining device may include, for example, a camera, a cellular phone with an embedded camera, or a computer. The imaging device can comprise hardware such as the image sensor and software for operating the image sensor and/or the imaging component. In some embodiments, the imaging device is incorporated or embedded in one of the other components of the system (e.g., the information processing component).

Communication Component

In some embodiments, the systems and methods comprise a communication component. In some embodiments, the communication component communicates information from the imaging device to an information processing component. In some embodiments, the communication component communicates information to or from the information processing component (e.g., to or from the imaging device). In some embodiments, the communication component communicates information from any one component of the system (e.g., an imaging component), to any other component of the system, between two sub-components of the system, or between a component outside of the system (e.g., subject device, administrator device, or third-party device). The communication component may communicate or facilitate communication of results and reports to the subject, federal and state agencies, subject's healthcare provider, and the like.

In some embodiments, a portion or all of the communication component is wired. For example, in some embodiments, the communication component comprises wires or cables connecting the imaging device directly or indirectly to an information processing component (e.g., computer, a computer processor within a phone, etc.).

In some embodiments, a portion of or the entire communication component is wireless. Any desired wireless communication technology may be employed, including but not limited to, electromagnetic wireless telecommunications (e.g., wireless networking, cellular, satellite), and electromagnetic induction (such as light, magnetic, or electric fields or the use of sound). Where wireless networks are employed, any desired protocol can be used (e.g., ZigBee, EnOcean, Personal area networks, Bluetooth, TransferJet, ultra-wideband).

In some embodiments, the imaging device comprises a wireless communication component such that signal generated from the imaging device is transmitted to an information processing component wirelessly in a HIPAA-compliant fashion. In some embodiments, the communication component communicates information comprising images and/or instructions to the information processing component.

Information Processing Component

In some embodiments, the systems and methods comprise an information processing component. The information processing component can provide a variety of functions, including but not limited to: receiving and processing images generated from the imaging device; receiving and storing demographics, symptoms, exposure details, or a combination thereof from the subject; receiving and storing test results; and displaying information, instructions, or questions to a subject.

In some embodiments, the information processing component comprises one or more of a computer processor, computer readable medium, and software. Any of a variety of computing devices may be used as the information processing component, including but not limited to, a desktop computer, a mainframe computer, a laptop computer, a personal digital assistant (PDA), a portable computer (e.g., mobile devices such as telephones), and a tablet computer (e.g., standard tablets, slates, mini tablets, phablets, customer handheld devices). In select embodiments, the information processing component comprises a tablet computer, or a portable computer.

In some embodiments, the information processing component, or a device in electronic communication with the information processing component (e.g., a video monitor), comprises a display. In some embodiments, the display displays textual and/or graphical information to a user (e.g., a subject completing a test or a test administrator). In some embodiments, the display is a touchscreen display, permitting the user to select and manage system functions via a graphical interface.

In some embodiments, the display displays information to the subject or test administrator related to instructions related to the test kit being used. In some embodiments, the display displays information to the subject or test administrator related to proper image capturing of the test result.

In some embodiments, the information processing component, or a device in electronic communication with the information processing component, comprises a networking component. The networking component receives and/or transmits information to the communication component.

In some embodiments, the information processing component comprises a database containing protocols, subject data, or other desired information. The protocols, subject data, or other desired information may be provided by computer processor, computer readable medium, software, or be available through a web-based platform via a web browser across the internet.

In some embodiments, the information processing component comprises an artificial intelligence component (e.g., embodied in software running on the processor). In some embodiments, the artificial intelligence component comprises image analysis software, as described elsewhere herein.

In some embodiments, the information processing component, the imaging component, the communication component, or any combination thereof are contained within a single device (e.g., a tablet computer, a mobile phone, and the like).

Protocol Component

In some embodiments, the systems and methods comprise a protocol component. The protocol component comprises instructions, typically embodied in software, for managing the methods and use of the system. The software comprises all non-transitory forms of software, or all those forms of software except those based on a transitory, propagating signal. In some embodiments, the protocol component is stored in a computer readable medium. In some embodiments, the protocol component is embodied in the information processing component.

In some embodiments, the protocol component directs the display of information. The information may be directed to guidance or instructions to the subject or test administrator (e.g., best practices based on lighting conditions, test manufacturer, lot number, etc.). In some embodiments, the display comprises instructions (e.g., graphical, textual, etc.) for use of the imaging component. For example, in some embodiments, the protocol component directs the subject or test administrator to repeat an image if quality is not acceptable. In some embodiments, the protocol component comprises specific protocols for the type of test kit being used.

In some embodiments, the protocol component comprises a query function, such that the protocol component displays questions regarding demographics, symptoms, or exposure details for the subject.

In some embodiments, the format of the display is adjustable to accommodate any subject type, including those with impaired vision or hearing, impaired cognitive skills, color blindness, young age, varied language skills or knowledge, etc.

The protocol component may be built on any desired hardware/software platform. In some embodiments, software components are provided via an application service provider (ASP) (e.g., are accessed by users within a web-based platform via a web browser across the internet; is bundled into a network-type appliance and run within an institution or an intranet; is provided as a software package and used as a stand-alone system; or is provided as downloadable software to a subject's device(s). The software components may be built on a system that comprises appropriate privacy and security features to comply with legal regulations regarding sharing and transferring of medical information.

The systems, methods, and readable media described herein protect the confidentiality and security of protected health information (PHI) in compliance with various patient privacy standards (e.g., Health Insurance Portability and Accountability Act (HIPAA)). Thus, the systems, methods and readable media may be considered HIPAA-compliant. The systems, methods and readable media may provide or allow one or all of: means of access control, mechanisms to authenticate electronic PHI, functionalities for encryption/decryption, and mechanisms to log activity and implement audits.

Any data or information in the disclosed methods may be communicated using known encryption/decryption and security techniques. For example, the systems, methods, and readable media may anonymize the subject or separate the subject demographics from the image prior to providing to image interpreters.

What is claimed is:

1. A computer implemented method for collecting, storing, and managing human readable diagnostic test results for a subject comprising:
   collecting demographics, symptoms, exposure details, or a combination thereof from the subject;
   receiving a test result for the subject, wherein the test result is a consensus result from a set number of initial image interpreters and a number of additional image interpreters as determined by a set of adjudication rules, wherein the number of additional image interpreters is based on the adjudication rules following results from the initial image interpreters; and
   storing the test result,
   wherein receiving the test result comprises:
   receiving on an information processing component, from a subject device or a test administrator device, one or more images of a test kit following use and test kit identification; and
   transferring the one or more images to a third-party device in contact with the initial image interpreters and additional image interpreters using a communication device within or in electronic communication with the information processing component wherein the initial image interpreters and additional image interpreters determine the test result, or
   transferring the one or more images to an image analysis component and determining the test result using image analysis software, or
   transferring the one or more images to an artificial intelligence component and determining the test result using the artificial intelligence component, or
   a combination thereof.

2. The method of claim 1, further comprising associating the test result with the subject.

3. The method of claim 1, further comprising collecting subject medical history.

4. The method of claim 1, wherein the medical history comprises vaccination records.

5. The method of claim 1, wherein the collecting comprises querying the subject in a protocol component.

6. The method of claim 1, wherein the collecting comprises identifying the subject demographics from an identification number, access code, or list of potential subjects.

7. The method of claim 1, wherein the test result is provided by the subject or a test administrator.

8. The method of claim 1, wherein the test result is a consensus result from at least three image interpreters.

9. The method of claim 1, further comprising providing the test result to the subject.

10. The method of claim 1, further comprising reporting the test result to state and federal health authorities.

11. A computer implemented method for collecting, storing, and managing human readable diagnostic test results for a subject comprising:
    collecting demographics, symptoms, exposure details, or a combination thereof from the subject;

receiving a test result from at least three image interpreters, wherein the test result is a consensus result from a set number of initial image interpreters and a number of additional image interpreters as determined by a set of adjudication rules;
associating the test result with the subject; and
storing the test result.

12. The method of claim 11, further comprising providing the test result to the subject.

13. The method of claim 11, wherein the collecting comprises querying the subject in a protocol component.

14. The method of claim 11, wherein the collecting comprises identifying the subject demographics from an identification number, access code, or list of potential subjects.

15. The method of claim 11, further comprising reporting the test result to state and federal health authorities.

16. The method of claim 11, further comprising collecting subject medical history.

17. The method of claim 11, wherein the medical history comprises vaccination records.

18. A non-transitory computer-readable medium storing instructions, that when executed by one or more processors performs operations comprising:
collecting demographics, symptoms, exposure details, or a combination thereof from a subject;
receiving one or more images of a test kit following use and test kit identification;
transferring one or more images to:
a third-party device in contact with more than one image interpreter using a communication device within or in electronic communication with the information processing component wherein the more than one image interpreter determines a test result, wherein the test result is a consensus result from a set number of initial image interpreters and a number of additional image interpreters as determined by a set of adjudication rules,
an image analysis component and determining the test result using image analysis software,
an artificial intelligence component and determining the test result using artificial intelligence software, or
a combination thereof;
receiving the test result for the subject; and
storing the test result.

19. The non-transitory computer-readable medium of claim 18, the operations further comprising:
querying the subject in a protocol component;
identifying the subject demographics from an identification number, access code, or list of potential subjects:
receiving on an information processing component, from a subject device or a test administrator device, an image of a test kit following use and test kit identification;
or a combination thereof.

20. The non-transitory computer-readable medium of claim 18, the operations further comprising one or more of:
associating the test result with the subject;
providing the test result to the subject;
reporting the test result to a governmental authority; and
collecting subject medical history.

21. A system comprising:
one or more processors; and
the non-transitory computer readable medium of claim 18.

* * * * *